United States Patent [19]

Todd et al.

[11] Patent Number: 4,962,023

[45] Date of Patent: Oct. 9, 1990

[54] SINGLE INCUBATION IMMUNO SORBENT ASSAY METHOD USING PARTICLE LABELS TO DETECT TEST ANTIGEN SPECIFIC ANTIBODIES IN PRESENCE OF OTHER ANTIBODIES

[75] Inventors: William J. Todd, Baton Rouge, La.; Paul A. Barstad, Frederick, Md.

[73] Assignee: Louisiana State University, Agricultural and Mechanical College, Baton Rouge, La.

[21] Appl. No.: 66,763

[22] Filed: Jun. 22, 1987

[51] Int. Cl.$^5$ .................. G01N 33/53; G01N 33/543; G01N 33/544; G01N 33/541

[52] U.S. Cl. ........................................ 435/7; 436/518; 436/524; 436/527; 436/528; 436/529; 436/530; 436/531; 436/540; 436/547; 436/800; 436/801; 436/804; 436/808; 436/828

[58] Field of Search .................... 435/7, 810; 436/518, 436/524, 527–531, 540, 547, 800, 801, 804, 808, 828; 424/3

[56] References Cited

U.S. PATENT DOCUMENTS 4,373,932  2/1983  Gribnau et al. ................ 422/61 X
4,486,530  12/1984  David et al. ................... 436/527 X

FOREIGN PATENT DOCUMENTS 158746  10/1985  European Pat. Off.

OTHER PUBLICATIONS

Voller, A., et al., In "Alternative Immunoassays" (W. P. Collins, ed), John Wiley & Sons, publisher, pp. 77–86 (1985).
Wide, L. In "Principles of Competitive Protein-Binding Assays", 2nd Edition (John Wiley & Sons, New York), Chapter 13, pp. 243–254.
Moeremans et al, "Sensitive Colloidal Metal (Gold or Silver) Staining of Protein blots on Nitrocellulose Membranes", Analytical Biochemistry, vol. 145, 1985, pp. 315–321.
Surek and Latzko, "Visualization of Antigenic Proteins Blotted onto Nitrocellulose using the Immuno-Gold-Staining (IGS) Method", Biochemical and Biophysical Research Communications, vol. 121, No. 1, 1984, pp. 284–289.
Romano and Romano, "Staphylococcal Protein A Bound to Colloidal Gold: A Useful Reagent to Label Antigen Antibody Sites in Electron Microscopy", Immunochemistry, 1977, vol. 14, pp. 711–715.
De Mey, "Colloidal Gold Probes in Immunocytochemistry":, Immunocytochemistry Practical Applications in Pathology and Biology, edited Polak and Van Noorden, 1983, pp. 82 and 83.
Frens, G., "Controlled Nucleation for Regulation of the Particle Size in Monodispersed Gold Suspensions", Nature Physical Science, vol. 241, 1973, pp. 20–25.
Langanger et al, "Ultrastructural Localization of alpha-Actinin and Filamin in Cultured Cells with Amino Gold Staining (IGS) Method", Journal of Cell Biology, vol. 99, Oct. 1984, pp. 1324–1334.
Handley et al, "Minireview–Colloidal Gold: A Pluripotent Receptor Probe", Proceedings of the Society for Experimental Biology and Medicine, vol. 174, 1983, pp. 1–11.
Lindmark et al, "Review Article: Binding of the Immunoglobulins to Protein A and Immunoglobulin Levels in Mammalian Sera", Journal of Immunological Methods, vol. 62, 1983, pp. 1–13.
Langone, John J., "Protein A of Staphylococcus Aureus and Related Immunoglobulin Receptors Produced by Streptococci and Pneumonococci", Advances in Immunology, vol. 32, 1982, pp. 200–206 and 232–234.
Goodman et al, "Colloidal Gold Markers and Probes for Routine Application in Microscopy", Journal of Microscopy, vol. 123, Part II, Aug. 1981, pp. 201–213.
Horisberger, Mark, "Colloidal Gold for a Cytochemical Marker in Electron Microscopy", Gold Bulletin, vol. 14, 1981, pp. 90–94.
Goodman et al, "A Review of the Colloidal Gold Marker System", Scanning Electron Microscopy, vol. II, 1980, pp. 133–145.
Faulk et al, "An Immunocolloid Method for the Electron Microscope", Immunochemistry, Communication to the Editors, vol. 8, 1971, pp. 1081–1083.
Janssen Life Sciences Products Brochure. Immunochemistry, 1984.

*Primary Examiner*—Jack Spiegel
*Attorney, Agent, or Firm*—Llewellyn A. Proctor; James M. Pelton

[57] ABSTRACT

An immunoassay method for one-step detection of specific antibodies which includes incubation of a solid phase support or matrix having a spot of the antigen bound thereto with a sample of the clinical fluid to be tested in the presence of a signal developing reagent, including a detector substance, which is preferably a colloidal metal sol, and a ligand, such as protein A or other antibody binding ligand. A diagnostic field kit containing the test antigens and signal developing reagent is also described.

19 Claims, No Drawings

SINGLE INCUBATION IMMUNO SORBENT ASSAY METHOD USING PARTICLE LABELS TO DETECT TEST ANTIGEN SPECIFIC ANTIBODIES IN PRESENCE OF OTHER ANTIBODIES

BACKGROUND OF THE INVENTION

This invention relates to an immunoassay method for detecting specific antibodies from biological fluid test samples using known antigens in a simple, reliable and efficient manner. More particularly, the present invention provides a single step procedure for detecting antibodies and reliably quantitating the concentration thereof without requiring a high level of skill by the test administrator. A field diagnostic kit for veterinary and human medical purposes or a professional office laboratory kit is included in the scope of the present invention.

Immunoassay or immunocytochemical assay methods have developed greatly over the past two decades. The many assay methods currently available to detect antibodies present in clinical specimens can generally be divided into two groups technically: (a) multi-step procedures, and (b) agglutination or precipitation type reactions. The multi-step procedures include many published assay methods using markers such as enzymes, radioactive labels, fluorescent labels, colloidal labels, or complement fixation. These methods require several steps to reach a definitive and lasting result, such as binding of antibodies to the target antigens, rinsing off unbound antibodies, and then detecting the remaining bound antibodies through the use of one of the labels. Subsequent preserving or mounting steps are also necessary in some cases. The agglutination and precipitation type reactions are dependent on and, therefore, limited to the detection of antibodies which have agglutinating or precipitating characteristics, are difficult to apply to more than one test antigen in a single procedure, and are relatively insensitive. Published reports of solid phase immunoassays using labeled colloidal gold or other labeled suspended particles to detect antibodies follow the long established, tedious and time consuming protocol and assay configuration that requires lengthy incubations of test sample to bind the antibodies, followed by a series of rinsing steps and at least one additional lengthy incubation with the colloidal label, see Moeremans et al, *J. Immunological Methods,* Vol. 74, 1984, pp. 353–360; Moeremans et al, "Sensitive Colloidal Metal (Gold or Silver) Staining of Protein Blots on Nitrocellulose Membranes", *Analytical Biochemistry,* Vol. 145, 1985, pp. 315–321; Surek and Latzko, "Visualization of Antigenic Proteins Blotted Onto Nitrocellulose Using the Immuno-Gold-Staining (IGS) Method", *Biochemical and Biophysical Research Communications,* Vol. 121, No. 1., 1984, pp. 284–289; and Yau-Heiu Hsu, "Immunogold for Detection of Antigen on Nitrocellulose Paper", *Analytical Biochemistry,* Vol. 142, 1984, pp. 221–225, to detect the antigen bound antibodies.

One visualization method for an immunoassay according to the general methodology of blot overlay assays using colloidal metal particles is shown in European Patent No. 158,746, published Oct. 23, 1985. This patent teaches the use of nitrocellulose paper as a blotting medium which is spotted with either tubulin or calmodulin, the remaining binding sites were quenched by incubating with bovine serum albumin (BSA), then the antigen containing nitrocellulose strips were incubated, respectively, with anti-tubulin and anti-calmodulin serum, followed by washing three times with BSA-Tris. Then the washed strips were incubated with the colloidal gold labeling material and again washed with BSA-Tris before evaluation. A comparison with an immobilized peroxidase incubation showed similar positivity, expressed differently however. Although the foregoing procedure employs a novel blot labeling technique, e.g., colloidal metal particle sols, the method itself is quite similar to the previously known enzyme labeled immunoassay method. This is seen from Example 1 in which the same method, using the two different labeling techniques, is run in side-by-side comparison and with similar results.

While the assay methods of the prior art provide accurate results, it is always desirable to achieve those results faster, with simpler and more reliable methods of increased sensitivity and at lower cost of both expensive biological materials and the analyst's labor. Therefore, it is an object of the present invention to provide an immuno-assay method which is simpler than the prior art procedures. A further object of the present invention is to provide an immunoassay method which is faster and allows very sensitive detection without instrumentation. Another object of the present invention is the provision of an immunoassay kit for field testing human and veterinary species or for use in a professional office laboratory. Other objects and advantages of the present invention will be apparent from the following description thereof.

THE INVENTION

The foregoing objects and advantages are provided by an immunoassay method for analyzing a test sample for test-antigen specific antibodies in the presence of non-test-antigen specific antibodies, which method comprises incubating a detecting amount of at least one known test antigen bound at a localized site on a solid phase substrate with a test sample in the presence of a signal developing reagent reactive with both said test-antigen specific antibodies and said non-test-antigen specific antibodies, so that a positive result for test-antigen specific antibodies in said test sample forms a signal at said site and a negative result is free from a signal at said site. A preferred signal developing reagent is a colloidal metal particle labeled ligand reactive with antibodies in the test sample. Most preferably, the antibody specific ligand coating the suspended particles is Staphyloccocal protein A labeled with colloidal gold.

Another feature of the present invention is provided by an immunoassay diagnostic kit for analyzing a test sample for test-antigen specific antibodies in the presence of non-test-antigen specific antibodies, which kit comprises (a) a solid substrate having bound thereto at a localized site a detecting amount of at least one known test-antigen for detecting a test-antigen specific antibody which may be contained in said test sample of interest; (b) a contained amount of a signal developing reagent reactive with both said test-antigen specific antibodies and said non-test-antigen specific antibodies; whereby incubation of said substrate with said test sample in the presence of said signal developing reagent causes formation of a signal at said site as a positive result for said test-antigen specific antibodies, and said site being free from a signal as a negative result for said test-antigen specific antibodies.

The immunoassay method of this invention includes an antigen which is the target of a specific antibody which may or may not be found in the biological fluid test sample. For purposes of this invention, the antibody which is targeting a bound antigen is referred to as a test-antigen specific antibody; all other antibodies which are not being sought are non-test-antigen specific antibodies. The antigen is usually provided in a relatively pure form, that is, without other competing antigens which would otherwise confuse or diminish the antigen-antibody reaction. Any identifiable antigen which may be fixed to the solid phase substrate and is reactive only with specific antibodies is suitable for the method of this invention. It is important to the invention that the antigen be bound to a solid phase or substrate. This feature of the invention enables easy evaluation, separation from assay reagents and preservation of the test results.

The solid phase or substrate can be any known substrate employed in conventional immunoassay procedures. Typically, such solid phase materials or substrates should be biologically neutral or converted to biologically neutral by blocking agents after attachment of the antigen to the solid phase; that is, they should bind the antigen sufficiently for purposes of the test, but not other components of the biological fluid test sample or the developing reagent. The solid phase materials or substrates employed in conventional and prior art immunoassay methods include membranes and paper such as nitrocellulose, nylon, Polysil, microporous plastic sheets (MPS), ZETA-PROBE, APT(2-aminophenylthioether) polystyrene, GENE SCREEN, diazotized membrane, blot absorbent membrane, or other support materials including beads, tubes, slides and the like. The preferred solid phase material or substrate is nitrocellulose paper because it is inexpensive, receives antigens and binds them suitably, but does not also bind other biological fluids or the colloidal label, especially when blocked directly after attachment of the antigens or later by blocking reagents present in the assay fluid, or using both methods, such as conveniently carried out as known in the art by use of bovine serum albumen (BSA), polyethylene glycol (PEG), gelatin, non-fat dry milk, and others as described herein below.

Typically, for nitrocellulose substrates, the antigen is spotted on the test strip in an amount sufficient for detecting by binding the complex of the antibody with the developing reagent. The amount of antigen spotted on the substrate should be sufficiently concentrated to show or indicate a positive response but not so concentrated as to prevent portions of the antigen from binding to the substrate and, thus, risk lifting off of the substrate during incubation. In general, an antigen spot from about 1 to about 5 millimeters in diameter containing about 1 to about 5 microliters of antigen material is useful in the method of this invention. However, higher or lower amounts are useful, but the color forming agent does not show as well at lower concentrations and amounts and higher concentrations and amounts are wasteful and unnecessary as well as tending to cause the antigen-antibody bound complex to lift off the solid substrate if several layers of antigen are present. Preferably, spots of one or more known antigens for detection of their corresponding antibodies, i.e., test-antigen specific antibodies, can be applied to a single substrate if the individual antigen spots are prevented from contacting one another. Thus, a test strip of the solid phase substrate containing a number of antigens, say 20 to 30 different antigens, can be used to test for the corresponding antibodies in a single test with accurate results and without interference from non-test-antigen specific antibodies binding in the test sample to the solid phase substrate.

The signal developing reagent is any convenient reagent which does not interfere with the binding of the test antigen and the test-antigen specific antibodies, which sufficiently binds to the test-antigen specific antibodies and which provides a conveniently perceivable signal or marker. Preferably, a complex of colloidal metal particles and Staphyloccocal protein A, both of which are known for binding with both test-antigen specific antibodies and non-test-antigen specific antibodies to develop a reddish color which can be detected microscopically and macroscopically. When used in the present method, detection by the unaided eye is easily accomplished. The developing reagent colors the antigen spot at the localized site on the substrate after only about 15 minutes and generally within 2 hours, providing a test strip or specimen with a clearly visible spot, if the appropriate antibody is present in the test sample. For samples which are diluted for specific antibodies prolonged incubation of 24 to 48 hours is acceptable because the assay reagents do not overdevelop or accumulate artifacts with time.

Although described specifically hereinabove, the signal developing reagent is generally a complex of a detector substance and a ligand capable of binding the detector substance to both the test-antigen specific antibodies and the non-test antigen specific antibodies. Preferably, the ligand is selected from protein ligands and substances termed anti-antibodies. It is only necessary that the ligand attach both the detector substance and the test sample antibodies.

The detector substance can be conveniently selected from a number of known signal agents or markers. For example, preferred detector substances are colloidal metal sols, radioactive labeled substances, fluorescent molecules, enzymes and combinations of these, which combinations sensitize and intensify the signaling effect.

The signal developing reagent includes, as the preferred detector substance, finely divided gold granules or particles which have been known and used previously for detection of antibodies in immunochemical procedures. See European Patent No. 158,746, supra. The finely divided granules can be produced and labeled according to several known procedures. The first reported procedure for protein A labeled colloidal gold markers was by Romano and Romano, *Immunochemistry*, Vol. 14, 1977, pp. 711–715. The three major methods of producing colloidal gold, also called monodisperse gold sols, are all based on controlled reduction of an aqueous solution of chloroauric acid using phosphorus-saturated ether as reducing agent for 3 nm and ±5 nm gold, sodium ascorbate for 10–15 nm gold, or sodium citrate for larger particles from 15–150 nm, see DeMey, "Colloidal Gold Probes in Immunocytochemistry", *Immunocytochemistry*, Practical Applications in Pathology and Biology, ed. Polak and Van Noorden, 1983, p. 82, 83. Thus, preferred particle sizes have a particle size range of 5 to 150 nanometers, and more preferably from about 15 to about 50 nanometers. Further, the concentration of colloidal metal is present at a concentration for the total surface area of said metal, preferably gold, to bind from about 0.5 to about 50 micrograms of the ligand per milliliter of said colloidal metal so and, more preferably, from 1 to about 50 micrograms per milliliter.

Another detector substance includes monodispersed, microparticles or microspheres produced from polymers, such as polystyrene and latex. These finely divided granules are known and have been previously used for detection of antibodies in immunochemical procedures in multistep processes, see Gridnau, T. C. J., et al, J. Chromotography, Vol. 376, 1984, pp. 175–189, and Bangs, L. B., "Uniform Latex Particles", Seragen Diagnostics, Inc., Indianapolis, Ind., 1984. They can be labeled with antibody binding ligands, such as protein A by adsorption at high pH and covalently by other known methods. Typically used particle sized granules range from about 0.05 to about 5.0 microns in diameter. Such polymer particles are commercially available from several manufacturers in a variety of colors or with fluorescent dyes, and pre-labeled with antibody binding ligands, such as protein A.

Both metal sol and polymer detector substances can be made radioactive or produced with attached enzymes or fluorescent markers for amplification of the antigen-antibody developed reaction signal.

Although specific methods have been referred to for colloidal gold, other heavy metals and metal compounds are also useful. Such other heavy metals and metal compounds typically include silver, platinum, gold, copper, silver iodide, silver bromide, copper hydrous oxide, iron oxide, iron hydroxide and the like. It is only desired that the particle size be small enough to act like a colloid, i.e., remain suspended in solution, or be easily re-suspended if the particles settle after long standing, that the particles react to bind to the antibodies either by themselves or with a complexing ligand such as a protein binding agent, such as Staphyloccocal protein A, Protein G, or anti-antibodies, all of which might be either monoclonal and polyclonal, and that a high enough concentration of the developing agent be present to bind substantially all the antibodies in the test sample, or sufficient to detect antibodies bound to the antigens on the substrate without effective competitive inhibition by antibodies present in the sample that are not specific for the antigen bound to the substrate. Because the binding affinity for protein A is higher for antibodies bound to their antigens than for free or unbound antibodies, the kinetics of the protein A reaction favors detection of the antibodies bound to their corresponding antigen placed on the solid phase substrate even in the presence of excess antibodies not specific for the chosen antigen. Protein A is therefore a preferred ligand to link the suspended detector substance particles to the antibodies bound to the antigens at a localized site on the solid phase substrate. Protein A is generally recognized as a convenient and efficient ligand for the colloidal gold and other suspended particulate detector substances and all sera of mammals contain antibodies which bind protein A. However, protein A is not effective for bird or fish sera.

The test sample which can be examined by the simplified method of the present invention includes practically any bodily fluid or clinical fluid which would contain antibodies to be detected. Typical bodily fluids include whole blood, blood serum, plasma, saliva, tears, clarified diarrhea, or dilutions thereof. Preferred is blood serum since it is easily available and requires only small amounts for test purposes. Typically, from 0.1 to 20 microliters of clinical or body fluid is sufficient for purposes of the test sample as used in the present invention. Serum dilutions ranging from about 1:100 to about 1:100,000 volume of fluid to volume of diluent remain sufficient for detection purposes, although the positive test become quite faint at the higher dilutions. The concentration of antibodies will have a slight affect on the test because it will affect the rate of color formation on the antigen spot on the solid phase substrate. Low level infections or infections that occurred long ago usually have a lower concentration of antibodies whereas a virulent or serious current or recent infection would have a proportionately higher concentration of antibodies. However, the concentration of antibodies is not a factor which the present invention can address since the test sample must be taken as it is found.

The conditions under which the present method is operated are important, but not critical, and are within a normal range for immunocytochemical tests in general. Typically, the incubation of the antigen-colloidal marker-antibody mixture will range from about fifteen minutes to several hours depending on concentrations of reagents, temperature and pH of the system. The temperature of the test method can range from about room temperature to physiological temperatures; that is, from about 25 to about 40° C. The rate of binding and positive response would increase proportionately with the temperature. However, at temperatures greater than about 40° C., the proteins and other biological materials begin to denature and otherwise lose their character. Further, increasing the concentration of antibodies can increase the rate of reaction until at some concentration inhibition by antibodies not specific for the test antigen will competitively inhibit the binding of the colloidal marker to the antigen, resulting in decreased efficiency of the assay. With protein A, the concentration at which inhibition occurs varies for each species of animal; however, because of high sensitivity, the assay can readily be conducted with amounts of serum and other biological fluids at antibody concentrations well below detectable competitive inhibition.

The method of the present invention will be more easily understood by reference to the following examples which are illustrative and non-limiting.

EXAMPLE 1

The solid phase substrate was prepared before the test procedure using ovalbumin protein as the antigen by attaching one microgram of ovalbumin to nitrocellulose paper. This was accomplished by applying one microliter of 0.05 M Tris buffer, pH 7.2, containing one milligram of ovalbumin per milliliter. The spot was vacuum dried and the remaining unbound nitrocellulose sites were blocked by brief incubation in one weight percent bovine serum albumin (BSA) followed by vacuum drying. The prepared nitrocellulose was stored at room temperature until used.

The developing reagent was prepared by reduction of gold chloride with sodium citrate as described by Frens, G., "Controlled nucleation for regulation of the particle size in monodisperse gold suspensions", *Nature Physical Science*, Vol. 241, 1973, pp. 20–22, which is incorporated by reference as if fully set forth, to provide colloidal gold particles of size desired from 15 nm to 150 nm. For this assay, colloidal particles of about 30 nm diameter were made and coated with Staphyloccocal protein A essentially by the method of Romano and Romano, supra, which is incorporated herein by reference as if fully set forth.

The test sera containing antibodies against ovalbumin protein were raised in a rabbit and obtained by subcutaneous injection of ovalbumin in Freund's incomplete adjuvant. Preinjection blood samples were obtained for controls, as well as, sera raised by the same methods against other antigens. All test samples were stored frozen until use.

The method of the present invention was carried out by adding 10 microliters of blood serum from a rabbit previously immunized with ovalbumin and a strip of nitrocellulose paper spotted with one microgram of ovalbumin to a test tube containing one milliliter of protein A coated colloidal gold developing reagent, all as previously prepared above. The tube was mixed by rocking at room temperature. After fifteen minutes, a red spot appeared at the site of the bound ovalbumin on the nitrocellulose strip, indicating a positive reaction and the presence of antibodies to ovalbumin in the test blood serum sample.

EXAMPLE 2

Ten microliters of blood from the rabbit used in Example 1 prior to exposure to ovalbumin and 10 microliters of blood from a different rabbit following the immunization protocol of Example 1 with a different antigen were treated following the procedure of Example 1 with another sample of positive ovalbumin serum in parallel. There was no red spot positive indication with the pre-immunization sample or the sample from the different rabbit and different antigen, while a red spot appeared on the parallel positive test. Incubation was continued overnight and the negative controls remained negative while the positive indication had turned a darker red.

EXAMPLE 3

Following the procedure of Example 1, the sensitivity of the test procedure was evaluated by the addition of smaller amounts of test sera to a series of 4 test tubes containing one milliliter of colloidal gold-protein A indicator and a test strip of ovalbumin spotted nitrocellulose paper. The results indicate that, at serum dilutions of 1:100, 1:500, 1:1200 and 1:2500, the color intensity of the indicator spot was proportional to the concentration of specific antibodies present and, thus, provides a quantitative indication of the antibodies present in the test sample.

EXAMPLE 4

The potential for non-specific antibodies to competitively inhibit the method of this invention through competition for the protein A binding sites on the colloidal gold indicator was evaluated by adding one microliter of positive rabbit serum to increasing amounts of control, i.e., rabbit serum negative for ovalbumin antibodies, then adding the total sera mixture to on milliliter of colloidal gold developing reagent in the presence of the ovalbumin spotted nitrocellulose paper strip. Positive indication, though faint, was detectable in the presence of even 200 microliters of blocking serum per microliter of positive serum. Because the amounts of undiluted sera, or other biological fluids high in antibody concentration, added per milliliter of colloidal gold indicator and solid phase antigen generally range from less than 1 microliter up to 50 microliters, competitive inhibition by antibodies present of specificity unrelated to the known test antigen is not significant. The reaction rate and intensity decreased with decreasing concentration of positive serum.

EXAMPLE 5

This Example illustrates the application of the described single step immunoassay to detect virus specific antibodies.

Equine Infectious Anemia (EIA) virus was chosen as the target antigen source. EIA virus was propagated in cultured equine fetal kidney cells. Virus released into the supernatant culture fluid was concentrated by ultrafiltration followed by centrifugation to form a small pellet of virus. Phosphate buffer, 0.05 M pH 7.4, was added in amounts just sufficient to resuspend the pellet and the suspended virus stock was stored frozen until used. The solid phase test antigen was made by adding 10 microliters of thawed virus stock to 90 microliters of 4 M KSCN. This step serves to disrupt the virus to expose internal as well as surface antigens. The disrupted virus was diluted 1:8 in 0.05 M Tris buffer, pH 7.2. To make the solid phase substrate, 1 microliter amounts of the diluted disrupted virus were individually spotted onto nitrocellulose paper. The spots were oven dried onto the nitrocellulose for 1 hour at 70 degrees centigrade. When prepared as described, one milliliter of virus concentrate would be sufficient to make 80,000 antigen spots. The solid phase supports, with the dots of attached virus antigens, were not blocked prior to use.

The signal developing reagent used was as described in Example 1, except that 2.5% w/v non-fat dry milk was added directly to the developing reagent as a blocker of non-specific reactions. Individual tests were made by placing 1 milliliter of protein A coated colloidal gold signal developing reagent along with a strip of nitrocellulose with one attached antigen dot into a test tube. To run the tests, 2.5 microliters of serum from a horse known to be EIA infected and known to be seropositive by the Coggins EIA test was added to one of the assay tubes and the same amount of serum from a known EIA negative horse was added to a second assay tube prepared in the same manner as the first tube as a control. After 15 minutes of incubation at ambient temperature, a red spot appeared at the antigen site of the positive serum indicating a positive reaction, and no color appeared at the antigen site of the negative control in the same time period. After continued overnight incubation, the antigen spot of the known positive serum was very dark red, while the antigen spot incubated with the negative serum was still negative, i.e., not colored, retaining the same white background of the nitrocellulose paper.

EXAMPLE 6

This Example illustrates the determination of serum titer by limiting dilution.

The same two sera and method of Example 5 were used in a standard serial dilution test to establish an end point reaction for the positive serum studies. Serial 1:5 dilutions of sera were made directly into the signal developing reagent containing 2.5% w/v non-fat dry milk. Dilutions ranging from 1:500 to 1:312,500 were assayed by overnight incubation at ambient temperature in the presence of the solid phase EIA antigen. Antigen dots incubated with dilutions of the known negative control sera were all negative, not colored. At a serum dilution of 1:62,500, the positive serum yielded a light red antigen spot indicating a weak positive reaction. The dilution of 1:62,000 was therefore taken as the end point for this serum specimen. At further levels of dilution, no color spot developed at the antigen site, indicating that the reaction antibodies had been diluted beyond the level of sensitivity of this test.

EXAMPLE 7

The effect of small volumes of developing reagent on the assay is illustrated in this Example.

To test if this single step assay could be run using the small fluid volumes required by some test configurations such as the commonly used 96 well microtiter plates, the nitrocellulose paper was cut circular, so that an antigen dot was located at the center, and the circles were placed, antigen spot upright, in the well bottoms of several wells of two 96 well microtiter plates. The wells of the microtiter plates used hold a maximum of 0.5 milliliters each. The same signal developing reagent used in Example 5 was added to the wells in amounts of 0.25 and 0.1 milliliters. The same positive and negative horse serum was added to separate wells using 1 microliter amounts. The results were recorded after 4 hours of incubation. All wells with positive serum contained a red color spot at the antigen site all wells with the negative control serum showed a white background at the antigen site. These results indicate it is possible to run this assay using only small amounts of reagents in test formats designed for automation.

EXAMPLE 8

The use of whole blood as the antibody source is illustrated in the following Example.

Whole blood was drawn from a known EIA seropositive horse and a known EIA seronegative horse in the presence of one of several anticoagulants. The three anticoagulants, heparin, citrate, and EDIA, were used separately as commercially available. After the whole blood was obtained, 1, 2.5, 5, 10, and 20 microliters were respectively removed from the blood of each horse collected in the presence of each anticoagulant, and were each separately added directly into a test tube containing 1 milliliter of the signal developing reagent similar to that used in Example 5 and EIA antigen dotted nitrocellulose strip. For convenience, the samples were incubated overnight at ambient room temperature. All samples from the known EIA positive horse showed a red spot at the antigen site indicating a positive reaction, and all samples incubated with blood from the known EIA negative horse remained white at the antigen site indicating negative reaction. Therefore, serum does not have to be separated from whole blood prior to assay with this antibody test. This observation enhances the value of the test especially under field conditions.

EXAMPLE 9

This Example illustrates an alternate signal developing reagent, i.e., the use of microspheres as a component of the signal developing reagent. To demonstrate the versatility of this single step assay, microspheres were used as an example of non-metal particles effective as part of the signal developing reagent.

Yellow-green Fluoresbrite microspheres, 0.21 microns in diameter, were purchased from Polyscience, Inc., of Warrington, Pa., and coated with protein A by overnight adsorption in carbonated buffer at pH 9.6. The protein A labeled spheres were separated from unbound protein A by pelleting the labeled spheres for 30 minutes at 10,000 RPM in a Sorval S-600 centrifuge head, and rinsing in 0.05 M Tris buffer pH 7.2. Prior to use, 2.5% w/v non-fat dry milk was added as a blocking agent. This colored and fluorescent microsphere indicator reagent was used in place of protein A labeled gold particles in Example 5, using similarly prepared positive and negative serum samples and protocol. After incubating 2.5 microliters of positive serum in the presence of 1 milliliter of microsphere containing signal developing reagent and the EIA antigen spotted nitrocellulose, a light yellow-green color developed at the antigen site, whereas no yellow-green color was detected at the antigen site of the negative control serum incubated in parallel with 1 milliliter of the same microsphere containing signal developing reagent. The reacted test strips were next assayed using ultraviolet light from a UVP, Inc., UV Transluminator. A very bright fluorescence was emitted from the EIA antigen site incubated with the positive serum, but not from the negative serum. The respective antigen spots were next observed by fluorescence microscopy. The antigen spot incubated with the positive serum emitted very bright light; the edge of the antigen spot was sharply determined. By fluorescence microscopy, some scattered background fluorescence was observed across the nitrocellulose. Microscopic examination of the antigen spot incubated with the negative serum only showed scattered nonspecific reactions across the surface of the nitrocellulose indicating a negative reaction. Fluorescence can be used to amplify a reaction.

Microspheres, also called monodispersed microparticles, in a variety of sizes, colors, organic chemical composition, and fluorescent stains can be obtained prelabeled with protein A and should be useful in signal developing reagents in this assay.

EXAMPLE 10

Application of the single step assay of this invention to detect antibodies specific for complex microorganisms is illustrated in this Example.

*Brucella abortus,* a major bacterial pathogen of cattle, infects a wide range of mammalian hosts including cattle, buffalo, elk, goats, and man. This microorganism was chosen as an example of a complex antigen target. The antigen, a crude extract of *B. abortus,* prepared according to the USDA published procedures, and known as the buffered brucella card test antigen, was diluted 1:80 in 0.05 M Tris buffer, pH 7.4 and 1 microliter amounts were spotted onto nitrocellulose paper to form the solid phase test antigen. The antigen was dried for 1 hour at 70 degrees centigrade. To prepare each test, a strip of nitrocellulose paper containing an antigen dot was placed in a test tube along with 1 milliliter of protein A coated colloidal gold signal developing reagent and 2.5% w/v non-fat dry milk, as described in Example 5. To run the assay, 2.5 milliliters of serum from a known seropositive cow were added to one of the prepared test tubes and 2.5 milliliters of serum from a known seronegative cow, as a control, were added to a second prepared test tube. After one hour of incubation at ambient temperature, a red spot appeared at the antigen site incubated with the known positive serum, indicating a positive test result, while the antigen site incubated with the known negative serum remained unstained, indicating a negative test result. This assay was repeated three times with the same test result.

From the above Example, it is seen that crude antigen preparations from complex microorganisms can function as antigens in this single step assay. The same reagents can be successfully applied to sera from different species. From the above Examples, it can be concluded that the assay as described functions for purified antigens, viruses as antigens and very complex sources of antigens such as microorganisms.

In another aspect of this invention, there is contemplated an assay method for detecting or quantitating a binding agent specifically reacting with an acceptor substance in which the acceptor substance is attached to a solid phase by contacting a test sample which may or may not contain the binding agent together with the localized acceptor substance in the presence of a marker linked to said binding agent. This procedure provides a marked indication at the localized site on the solid phase when the specific binding is present in the test sample and is free from marker indication when the specific binding agent is absent from the test sample. Although previously disclosed above in reference to the antigen-antibody immunoassay test, it is believed that the scope of the invention extends to other systems under this aspect of the invention. Typically, various polypeptides, including proteins, enzymes, hormones, and the like, have a specific tertiary structure which provides a definite recognition or active binding site. In some cases, a variety of other influences, such as substrate inhibition and competitive inhibition, affect binding of various substances with the polypeptides, but in other cases, the substances are specific to one other polypeptide or other substance for binding to the active site. Typical of such situations are a protein of a peptide specific to a virus, or other microorganism a carbohydrate characteristic of a microorganism or certain constituents of certain biological tissues. Thus, all of these constitute antigens or have the ability to raise specific antibodies which can then be detected or quantitated according to the method of the present invention. Thus, a simple, reliable test method for viruses which are human pathogens, such as rubella virus; herpes virus, including herpes simplex, herpes zoster, cytomegalo virus or Epstein Barre virus; the AIDS virus, including the HIV, LAV or HTLV-III viruses. Also, tests are included for viruses which are animal pathogens, such as feline leukemia virus or equine infectious anemia virus; for microorganisms pathogenic to either humans or animals, such as *Brucella abortus, Toxoplasma gondii,* and the like. The antigen can also be a normal or aberrant constituent of blood serum or other tissues. As such, the antigen is obtainable from normal sources, produced by infected cells, or synthetically, by chemical synthesis or recombinant DNA techniques to produce synthetic antigens such as polypeptides or carbohydrates.

For a diagnostic kit, it is only necessary to prepare suitably spotted nitrocellulose strips, having appropriately identified spots of antigens, a container of labeled suspended particle signal developing reagent and a means of obtaining a suitable test sample of clinical fluid. Clean test tubes or other suitable containers are made available as required. Thus, a field diagnostic immunocytochemical assay kit and method of the present invention for human or veterinary species is conveniently produced. In a similar fashion, a diagnostic kit for a professional's office laboratory is also provided. The only step for the practitioner is to add a predetermined amount of assay fluid, such as blood serum, and then to read the visually apparent result after an appropriate period of incubation a predetermined for each type of test.

Having described the present invention, one skilled in the immunoassay art will readily envision changes and variations in the invention which are nevertheless within the spirit and scope thereof. Accordingly, it is desired that the present invention be limited only by the lawful scope of the following claims.

What is claimed is:

1. An immunoblot assay method for analyzing a test sample for the detection of test-antigen specific antibodies in the presence of non-test-antigen specific antibodies, which comprises binding a detecting amount of at least one known test antigen to a localized site on a solid phase substrate;

immersing said solid phase substrate, to which said antigen is bound, in a signal developing reagent reactive with both said test-antigen specific antibodies and said non-test-antigen specific antibodies sufficient to label both the test-antigen specific antibodies and the non-test-antigen specific antibodies;

adding the test sample, which contains both test-antigen specific antibodies and non-test-antigen specific antibodies to said signal developing reagent and said immersed solid phase substrate, to which said test antigen is bound, incubating in a single step to form a single reaction mixture; incubating said mixture; and detecting a signal in said reaction mixture produced by said signal developing reagent, wherein a positive result for test-antigen specific antibodies in said test sample is indicated by localization of said signal in said reaction mixture at said substrate bound test antigen site.

2. The method of claim 1 in which said known antigen is deposited as a blot on a suitable solid phase substrate.

3. The method of claim 1 wherein said substrate to which said test antigen is bound is further characterized as being selected from the group consisting of nitrocellulose, nylon, ZETA-PROBE, APT(2-aminophenylthioether) polystyrene, GENE SCREEN, diazotized membrane, blot adsorbent membrane, beads, tubes, and slides.

4. The method of claim 3 wherein said substrate is nitrocellulose.

5. The method of claim 1 wherein said signal developing reagent is a complex of a detector substance and a ligand binding said detector substance to both said test-antigen specific antibodies and said non-test-antigen specific antibodies.

6. The method of claim 5 wherein said ligand is selected from the group consisting of protein ligands and anti-antibodies.

7. The method of claim 6 wherein said ligand is a protein ligand selected from the group consisting of Staphyloccocal protein A and protein G.

8. The method of claim 7 wherein said ligand is Staphyloccocal protein A.

9. The method of claim 5 wherein said detector substance is selected from the group consisting of colloidal metal sols, fluorescent material, enzymes, and combinations of one or more such detector substances.

10. The method of claim 9 wherein said detector substance is a colloidal metal sol.

11. The method of claim 10 in which the metal of said colloidal metal sol is selected from the group consisting of metal particles and metal compounds selected from platinum, gold, silver, copper, silver iodide, silver bromide, copper hydrous oxide, iron oxide and iron hydroxide.

12. The method of claim 11 in which said colloidal metal sol is a colloidal gold sol.

13. The method of claim 12 wherein said colloidal gold sol is a particulate material of particle size ranging from about 5 to about 150 nanometers diameter.

14. The method of claim 9 wherein said detector substance is a fluorescent material which is a polymer microsphere having a fluorescent stain.

15. The method of claim 5 in which said signal developing reagent is present at a concentration sufficient to bind substantially all of both said test-antigen specific antibodies and said non-test-antigen specific antibodies.

16. The method of claim 15 in which the detector substance of said signal developing reagent is a colloidal metal sol which is present at a concentration for the total surface area of said metal to bind from about 0.5 to about 50 micrograms of said ligand per milliliter of said colloidal metal sol.

17. The method of claim 16 wherein the concentration is in the range of colloidal metal present in about 1.0 to about 50 microliters per milliliter of colloidal metal sol.

18. The method of claim 1 wherein the amount of said test sample used in said immunoblot assay method is in the range of about 0.1 to about 20 microliters.

19. The method of claim 1 wherein said incubating is carried out for a period of about 0.25 to about 24 hours and at a temperature of from about 20 to about 37° C.

* * * * *